United States Patent [19]
Huebner et al.

[11] Patent Number: 5,562,672
[45] Date of Patent: Oct. 8, 1996

[54] TAPERED BONE SCREW WITH CONTINUOUSLY VARYING PITCH

[75] Inventors: Randall J. Huebner, Aloha; Gene L. Conrad, Beaverton, both of Oreg.

[73] Assignee: Acumed, Inc., Beaverton, Oreg.

[21] Appl. No.: 332,445

[22] Filed: Oct. 31, 1994

Related U.S. Application Data

[63] Continuation of Ser. No. 7,196, Jan. 21, 1993, abandoned.
[51] Int. Cl.⁶ ........................................... A61B 17/86
[52] U.S. Cl. .......................... 606/73; 411/307; 411/415
[58] Field of Search ........................ 606/65, 73, 72; 623/16; 411/415, 423, 426, 307, 310, 311, 411

[56] References Cited

U.S. PATENT DOCUMENTS

| | | | |
|---|---|---|---|
| 65,651 | 6/1867 | Davies | 411/415 |
| 146,023 | 12/1873 | Russell . | |
| 2,801,631 | 8/1957 | Charnley | 128/92 |
| 3,079,181 | 2/1963 | Van Der Wissel | 411/307 X |
| 3,124,408 | 3/1964 | Oestereicher | 411/415 X |
| 3,454,070 | 7/1969 | Phipard | 411/307 X |
| 4,175,555 | 11/1979 | Herbert | 128/92 |
| 4,863,383 | 9/1989 | Grafelmann | 433/174 |
| 4,950,270 | 8/1990 | Bowman et al. | 606/72 |
| 5,019,078 | 5/1991 | Perren et al. | 606/61 |
| 5,120,171 | 6/1992 | Lasner | 606/73 X |
| 5,403,136 | 4/1995 | Mathys | 411/310 |

FOREIGN PATENT DOCUMENTS

| | | | |
|---|---|---|---|
| 731381 | 4/1966 | Canada . | |
| 1007493 | 3/1977 | Canada | 411/415 |
| 3630863 | 3/1988 | Germany | 606/73 |
| 365613 | 12/1938 | Italy . | |
| 45-24729 | 8/1970 | Japan | 411/411 |
| 0077837 | 6/1918 | Switzerland | 411/415 |
| 1216466 | 3/1986 | U.S.S.R. | 411/307 |
| 0598834 | 2/1948 | United Kingdom | 411/411 |
| WO89/09030 | 10/1989 | WIPO . | |
| 9300518 | 1/1993 | WIPO | 411/310 |

OTHER PUBLICATIONS

The Herbert™ Bone Screws for Small Bone Fractures, Fracture Management, 97–1152–01 12.5MI Printed in U.S.A. ©1992 Zimmer, Inc.

*Primary Examiner*—David H. Willse
*Attorney, Agent, or Firm*—Marger, Johnson, McCollom & Stolowitz, P.C.

[57] ABSTRACT

A bone screw having a continuously varying pitch includes a tapered root portion having a relatively small diameter on a leading end of the screw and a larger trailing diameter. The pitch of the screw decreases between the leading and trailing ends thus causing the bone fragments in a fracture to be drawn together when the screw is installed across the fragments. The radially outer diameter of the threads increases between the leading and trailing ends thus causing each successive thread portion to cut into bone radially outwardly from the preceding thread portion thereby providing uncut bone in which the succeeding threads can gain purchase.

3 Claims, 3 Drawing Sheets

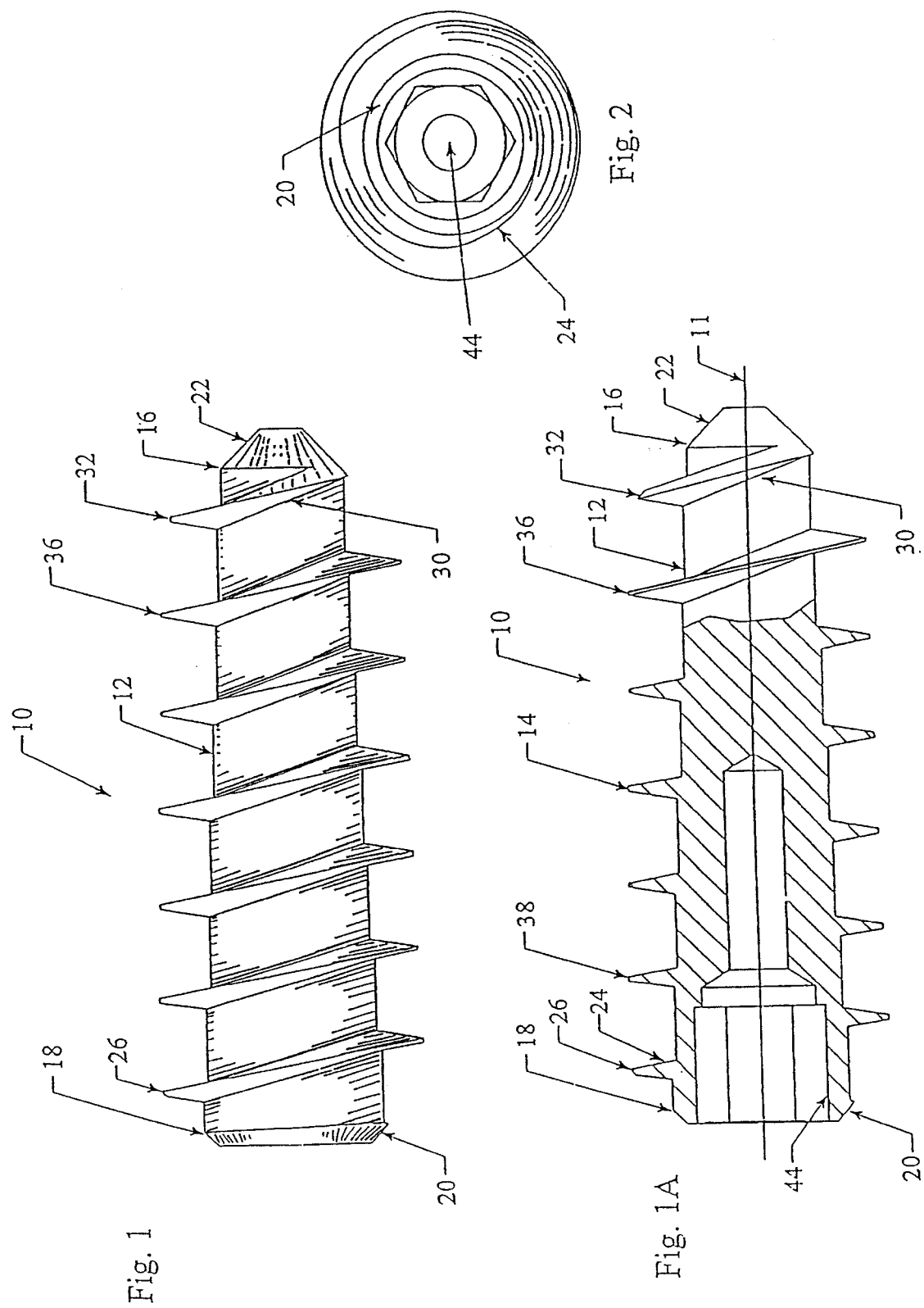

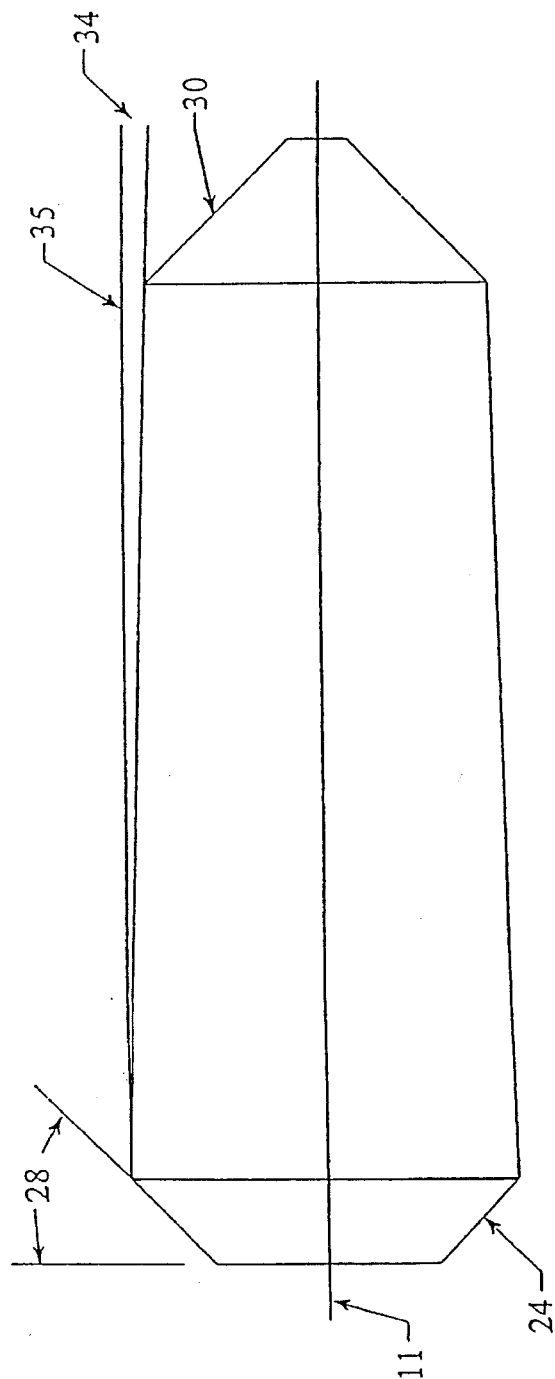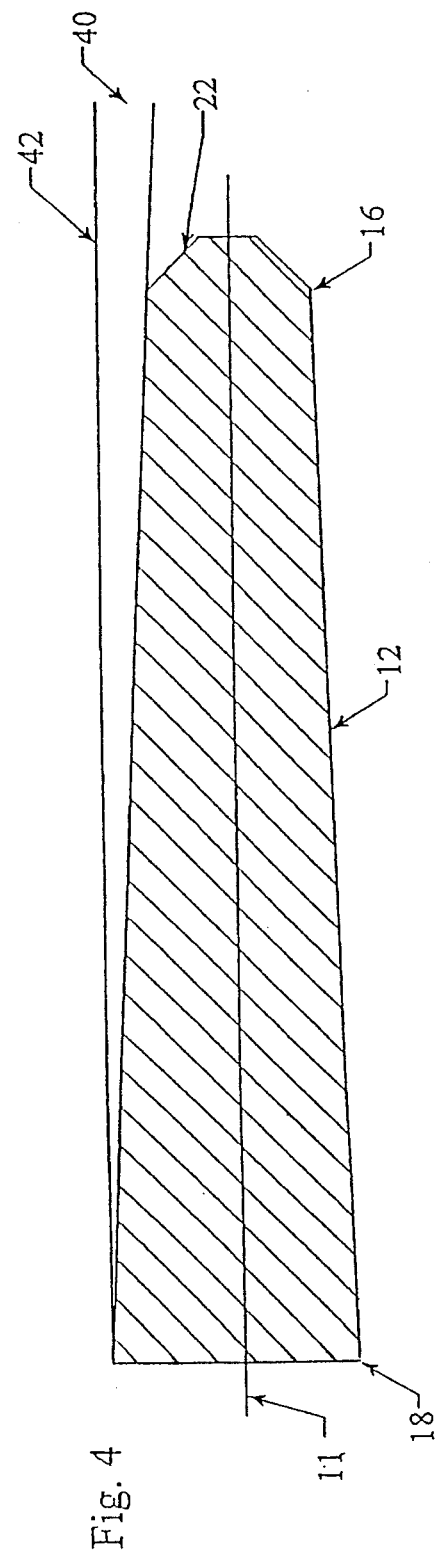

TAPERED BONE SCREW WITH CONTINUOUSLY VARYING PITCH

This is a Continuation of application Ser. No. 08/007,196 filed Dec. 21, 1993, now abandoned.

BACKGROUND OF THE INVENTION

1. Field of the Invention

The present invention relates generally to a bone screw for drawing together portions of a bone separated by a fracture and more particularly to such a screw which draws the bone portions together as a result of different-pitched threads on the screw.

2. Description of the Related Art

In healing bone fractures it is desirable to compress the fractures so that the fractured surfaces are pressed against one another. In the prior, art bone screws have been used to draw the fractured surfaces together and thereby optimize the healing process.

A number of prior art bone screws are constructed in similar to wood screws. For example, some prior art bone screws include a threaded distal portion and a head having a relatively long unthreaded shank disposed between the head and the distal portion. A drill is used to bore a hole through the fracture and the screw is threaded into the remote bone fragment with the head of the screw compressing the near fragment tightly against the remote bone fragment.

Other bone screws are threaded along the length thereof thus requiring a first drill bit to bore a hole in both bone fragments across the fracture and a second bit to drill a larger hole in the near bone fragment so that the screw threads do not engage the near bone fragment. Thereafter, the screw is tightened in the same manner as described above in connection with the screw having an unthreaded shank thereby compressing the fragments together.

Another bone screw is described in U.S. Pat. No. 4,175,555 to Herbert. The Herbert bone screw includes a shaft having leading and trailing portions with a first screw thread formed on the leading portion. A second screw thread is formed on the trailing portion which is like-handed but of a smaller pitch than the first screw thread. A slot or hex socket is formed on the trailing portion to accommodate a driver for driving the screw into a bore formed across a bone fracture.

As noted in the Herbert patent, bone screws having heads suffer from several disadvantages including concentrated loads beneath the screw head and the provision of the screw head itself after the screw is installed. Several other shortcomings of the standard type of bone screw are detailed in the Herbert patent.

The Herbert bone screw is advantageous in that it eliminates a conventional screw head on the trailing end portion of the screw. The Herbert bone screw, however, itself suffers from a number of disadvantages.

In the Herbert screw, the leading threads have a smaller diameter than the trailing threads. This is necessary to permit the leading threads to pass through the relatively large bore in the near bone fragment and engage the smaller bore in the remote bone fragment. The larger trailing threads then engage the larger bore in the near bone fragment. As a result of this arrangement, any stripping of the threads cut into the bones during installation of the screw occurs in the remote bone. If the stripping occurred in the bore in the near bone fragment, a screw having a head thereon could still be used to compress the fracture even though the near bore was stripped; however, when stripping occurs in the bore in the remote bone, a standard screw with the head thereon cannot be used and another bore must be drilled.

Further, the Herbert screw must be correctly positioned, i.e., it is imperative that the fracture intersect the unthreaded central portion of the Herbert bone screw when the same is installed. In addition, because the Herbert screw is not threaded entirely along the length thereof, the purchase obtained by the screw in the bone is not as good as with a screw threaded along the entire length. Also, two bores of different sizes must be drilled to install the Herbert screw rather than a single bore.

It would be desirable to provide a headless bone screw which overcomes the disadvantages associated with the Herbert bone screw.

SUMMARY OF THE INVENTION

A bone screw for drawing together portions of a bone separated by a fracture includes a root portion having a leading end and a trailing end. The leading end has a smaller diameter than the trailing end. A screw thread is formed on the mot portion between the leading and trailing ends and has a pitch which varies along the length thereof. The thread is adapted to thread in the cancellous material of the respective bone portions to be joined by the screw. Means are provided on the trailing end of the root portion to accommodate a tool for driving the screw. The present invention also contemplates a method for drawing together portions of a bone separated by a fracture.

The foregoing and other objects, features and advantages of the invention will become more readily apparent from the following detailed description of a preferred embodiment which proceeds with reference to the drawings.

BRIEF DESCRIPTION OF THE DRAWINGS

FIG. 1 is an enlarged side elevation view of a bone screw constructed in accordance with the present invention.

FIG. 1A is a view of the screw of FIG. 1 shown partially in cross section.

FIG. 2 is an end view of the bone screw of FIG. 1.

FIG. 3 is a drawing illustrating the outside diameter of the screw.

FIG. 4 is a drawing illustrating the diameter of the root portion of the screw.

DETAILED DESCRIPTION OF THE PREFERRED EMBODIMENT

Figure 5:
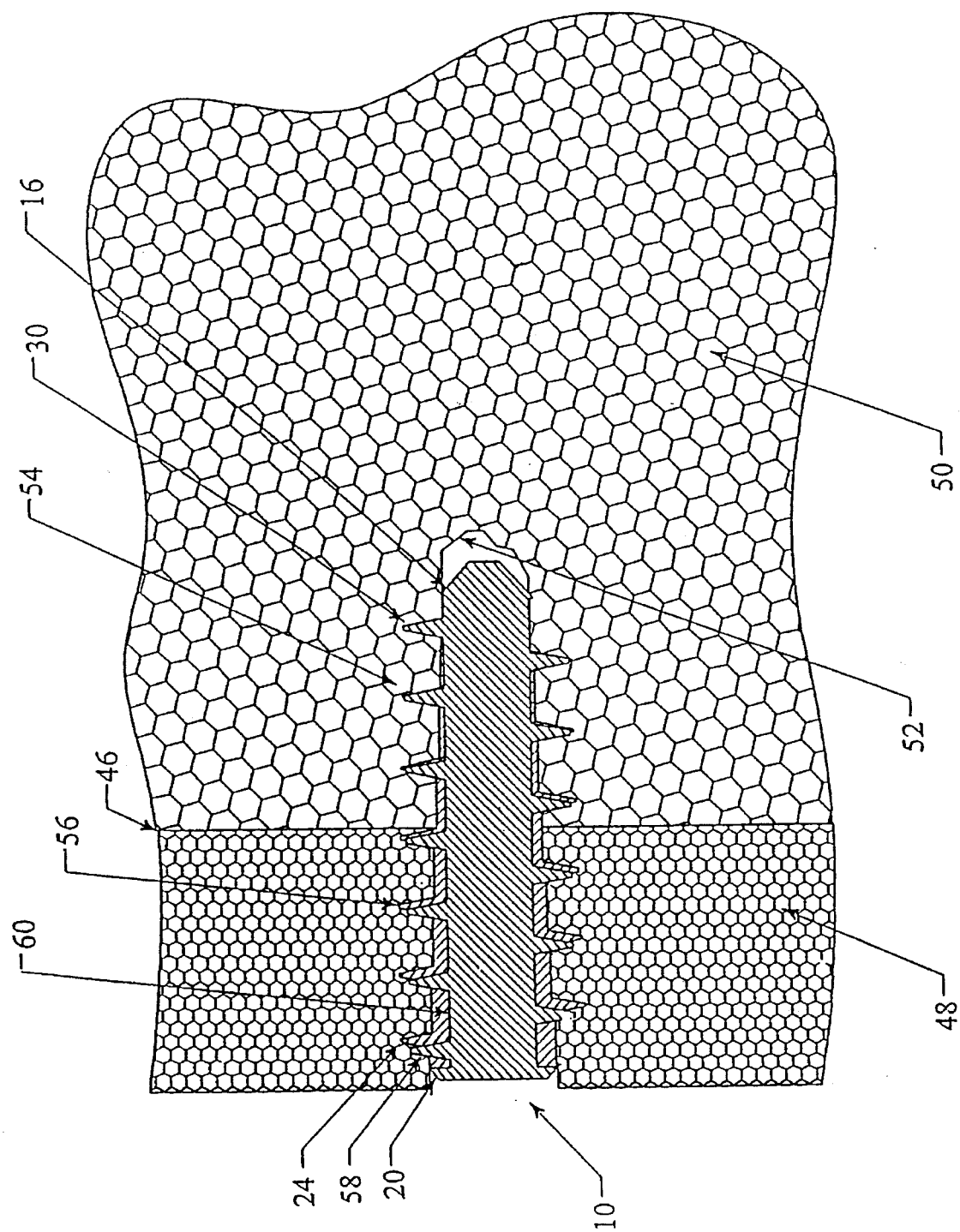
FIG. 5 is a cross-sectional view of a bone screw constructed in accordance with the present invention installed in a bone to draw a fracture together.

Indicated generally at 10 in FIGS. 1 and 1A is a bone screw constructed in accordance with the present invention. Bone screw 10 is centered on a longitudinal axis 11. The length of screw 10 as measured along axis 11 is 0.394 inches in the present embodiment of the invention. The bone screw includes a root portion 12 having a continuous screw thread 14 formed thereon.

Root portion 12 includes a leading end 16 and a trailing end 18. As can best be seen in FIG. 4, the diameter of leading end 16 is less than the diameter of trailing end 18. Also in FIG. 4, it can be seen that root portion 12 tapers between trailing end 18 and leading and 16. A 45° bevel 20, in FIGS.

1 and 1A, is formed on trailing end 18. In the present embodiment of the invention, trailing end 18 has a diameter of approximately 0.092 inches. A frusto-conical nose portion 22 is formed on leading end 16 of root portion 12. Screw thread 14 extends continuously between nose portion 22 and bevel 20. As can be seen in FIGS. 2 and 3, a trailing thread 24 has a crest height, i.e., the distance between axis 11 and a crest 26 of trailing thread 24, which varies so as to form a substantially 45° angle, illustrated as angle 28 in FIG. 3, between the outside diameter of crest 24 and axis 11.

A similarly tapering leading thread 30 also has a crest 32 which varies in height over a first partial turn of screw thread 14 so as to form an angle of substantially 45° with axis 11 as illustrated in FIG. 3.

The crest of screw thread 14 between trailing and leading threads 24, 30 respectively, varies in height along the length of thread 14. In the present embodiment of the invention, the outside diameter defined by the crest of thread 14 between the leading and trailing threads forms an angle 34, in FIG. 3, of approximately 1.43° with respect to an axis 35 extending from the radially outermost portion of thread 14 parallel to axis 11. In the present embodiment of the invention, the diameter of the radially outermost portion of thread 14 is approximately 0.138 inches.

The pitch of thread 14, i.e., the distance from one point on the thread to the corresponding point on an adjacent thread measured parallel to axis 11, decreases between the leading and trailing ends of the screw. For example, in the present embodiment of the invention, the distance between the uppermost portion of crest 32 in FIG. 1A and a corresponding crest portion 36 is 0.04964 inches. The distance between the uppermost portion of crest 26 and a corresponding crest portion 38 is 0.04748 inches. In the present embodiment of the invention, the pitch change per revolution is approximately 0.00036 inches.

The pitch depth, i.e., the distance between the crest and the radially outer surface of root portion 12 similarly varies along the length of the screw. In the present embodiment of the invention, the pitch depth where leading thread 30 joins the remainder of screw thread 14 is approximately 0.0302 inches. The pitch depth where trailing thread 24 joins the remainder of thread 14 is approximately 0.0240 inches.

The decrease in pitch depth between the leading end and trailing end of the screw can be seen by comparing FIG. 3 and FIG. 4 wherein root portion 12 tapers more sharply from the trailing to the leading end of the screw than does the change in crest height as shown in FIG. 3. In the present embodiment of the invention, the outside diameter of root portion 12 between leading and trailing ends, 16, 18, respectively, forms an angle 40, in FIG. 4, of approximately 2.5° with respect to an axis 42 extending from the radially outermost portion of trailing end 18 parallel to axis 11.

A hex socket 44 is formed on the trailing end of screw 10 to accommodate a driver as will be hereinafter further explained in connection with a description of the procedure in which the screw is used to draw opposing fragments of a fractured bone together.

Turning now to FIG. 5, illustrated therein is a fracture 46 which separates adjacent bone portions 48, 50. Screw 10 is illustrated installed in a bore 52 which extends through bone portions 48, 50 across fracture 46.

In installing screw 10, a surgeon first drills bore 52 across bone portions 48, 50 as shown. The bit may be a conventional cylindrical bone bit or may comprise a bit having a slight taper from the leading to the trailing end thereof. Thereafter, the surgeon inserts a tool (not shown) having a hex driver extending therefrom which is connectable to hex socket 44 for screwing screw 10 into bore 52. Bore 52 is of a size to just receive leading end 16 of screw 10. As soon as nose portion 22 is received within the bore, torque is applied using the tool inserted into hex socket 44 thereby causing leading thread 30 to cut into the bone adjacent bore 52.

In the view of FIG. 5, screw 10 is hatched to show the path cut by leading thread 30 after screw 10 is installed in the position illustrated in FIG. 5. The path of thread 30 is depicted using hatching, like hatching 54, 56, 58 which indicates the position of the path cut by leading thread 30 relative to succeeding threads of the screw. Hatching 60 depicts the actual position of the thread on screw 10 and root 12. It is to be appreciated that hatching 54, 60 are not used in FIG. 5 to depict different structure, which is unitary as illustrated in FIG. 1, but to depict relative positions of the path cut by leading thread 30 and the actual position of subsequent threads in the installed screw.

Because of the decreasing pitch along the length of the screw, each successive thread received in the path cut by thread 30 exerts pressure against the left side (as viewed in FIG. 5) of the path cut by thread 30 thereby tending to compress the bone along the length of the screw. As can be seen in FIG. 5, by the time the screw is fully installed, trailing thread 24 compresses a substantial amount of bone when it is received in the path cut by thread 30. This tends to draw bone portions 48, 50 tightly together across fracture 46 thereby promoting healing of the fracture.

As can be appreciated from the view of FIG. 5, the taper is important for two reasons. First, each succeeding portion of the thread is spaced further radially outwardly as a result of the taper and therefore the outer or portion of each thread (that portion closely adjacent the crest) cuts into new bone which was not cut by the preceding thread. This provides a much better purchase than would a thread having a continuously varying pitch on a cylindrical root. In such a configuration, each succeeding thread cuts additional bone within the generally cylindrical volume defined by the outside diameter of the threads. The outer portion of each thread (that portion closely adjacent the crest) therefore cuts into bone also cut by the preceding thread.

The tapered root is also advantageous in that the radially outer surface of the root, i.e., that portion between adjacent threads, is tightly urged against uncut bone defining the wall of bore 52. It is desirable for all surfaces of screw 10 to be tightly urged against adjacent bone, rather than a space cut by a thread, in order to increase purchase of the screw.

Having illustrated and described the principles of our invention in a preferred embodiment thereof, it should be readily apparent to those skilled in the art that the invention can be modified in arrangement and detail without departing from such principles. We claim all modifications coming within the spirit and scope of the accompanying claims.

We claim:

1. A screw comprising:

a root portion having a leading end and a trailing end, said root portion having a substantially constant tapered surface formed between a smaller diameter portion at said leading end and a larger diameter portion at said trailing end;

a screw thread formed on said tapered surface and having a pitch measured between substantially all corresponding points of consecutive threads which substantially uniformly varies between a larger pitch at said leading end and a smaller pitch at said trailing end, said thread having a pitch depth which is larger at the leading end of said screw than at the trailing end thereof and which varies substantially uniformly along the length of said screw thread;

a crest formed on said screw thread, said crest having a height measured from the longitudinal axis of said screw which is smaller at the leading end of said screw thread than at the trailing end thereof and which varies substantially uniformly along the length of said screw thread, said crest further having an outside diameter which includes the widest portion of said screw and which extends substantially beyond said root portion; and means on the trailing end of said root portion to accommodate a tool for driving the screw.

2. The screw of claim 1 wherein said screw is a headless screw and wherein said root portion trailing end comprises the rear most portion of said screw.

3. The screw of claim 2 wherein said screw thread is formed on substantially all of said root portion.

* * * * *